United States Patent [19]

Matsumoto et al.

[11] Patent Number: 5,302,393
[45] Date of Patent: Apr. 12, 1994

[54] METHOD FOR INHIBITING BIOLOGICAL DEGRADATION OF IMPLANTATION POLYMERIC MATERIAL, INHIBITOR THEREOF AND IMPLANTATION POLYMERIC MATERIAL CONTAINING THE INHIBITOR

[75] Inventors: Hiroshi Matsumoto, Tokyo; Kensuke Kondo; Kazuhiko Inoue, both of Hyogo; Nobutaka Tani, Osaka, all of Japan

[73] Assignee: Kanegafuchi Kagaku Kogyo Kabushiki Kaisha, Osaka, Japan

[21] Appl. No.: 910,809

[22] Filed: Jul. 9, 1992

[30] Foreign Application Priority Data

Jul. 11, 1991 [JP] Japan .................................. 3-171063
Aug. 2, 1991 [JP] Japan .................................. 3-194169

[51] Int. Cl.$^5$ ............... A61M 39/00; A61L 27/00; A61K 31/74
[52] U.S. Cl. ......................... 424/423; 424/426; 600/36; 606/231; 623/11
[58] Field of Search ............... 544/256; 514/258; 424/423, 426, 428

[56] References Cited

U.S. PATENT DOCUMENTS

| | | | |
|---|---|---|---|
| 4,427,648 | 1/1984 | Brickl et al. ........................ | 514/258 |
| 4,627,836 | 12/1986 | MacGregor ........................ | 424/423 |
| 4,629,621 | 12/1986 | Snipes ............................... | 428/402.24 |
| 4,676,975 | 6/1987 | McGary et al. .................... | 424/423 |
| 5,010,064 | 4/1991 | Fregnan et al. ................... | 514/258 |

FOREIGN PATENT DOCUMENTS 2812174 3/1978 Fed. Rep. of Germany .
2399836 7/1978 France .

OTHER PUBLICATIONS

Ann. Thorac. Surg., vol. 44, No. 4, Oct. 1987, pp. 398–403; M. N. Ilbawi et al.: "Valve replacement in children: guidelines for selection of prosthesis and timing of surgical intervention".
S. Afr. Med. J., vol. 63, No. 26, Jun. 25, 1983, pp. 997–1006; P. Jacobs et al.: "Review article: The antithrombic drugs in clinical practice".
Makromol. Chem., No. 5, Apr. 1981, pp. 15–29, Basel, CH; W. Marconi: "New nonthrombogenic polymer compositions".

Primary Examiner—Thurman K. Page
Assistant Examiner—Peter F. Kulkosky
Attorney, Agent, or Firm—Sughrue, Mion, Zinn, Macpeak & Seas

[57] ABSTRACT

A method for inhibiting decomposition and/or degradation of an implantation polymeric material in the living body, which comprises allowing dipyridamole and/or a salt or a derivative thereof as an active component to exist in the vicinity of an implantation polymeric material implanted in the living body; an inhibitor effective for inhibiting biological decomposition and/or degradation of a polymeric material implanted in the living body, which comprises dipyridamole and/or a salt or a derivative thereof as an active component; and an implantation polymeric material which contains dipyridamole and/or a salt or a derivative thereof as an active component.

16 Claims, No Drawings

METHOD FOR INHIBITING BIOLOGICAL DEGRADATION OF IMPLANTATION POLYMERIC MATERIAL, INHIBITOR THEREOF AND IMPLANTATION POLYMERIC MATERIAL CONTAINING THE INHIBITOR

FIELD OF THE INVENTION

This invention relates to a method for inhibiting biological decomposition and/or degradation of a polymeric material implanted in a living body, to an inhibitor thereof and to a polymeric material for implantation in the living body which exhibits minimal decomposition.

BACKGROUND OF THE INVENTION

In view of the rapid progress in the development of medical techniques in recent years, a variety of medical devices are currently implanted in the living body for a prolonged period. In particular, polymeric materials have been actively developed as materials for implantation in the living body (to be referred to as "implantation material" or "implantation polymeric material" hereinafter), because their mechanical properties are closer to those of biological components than those of metals, ceramics and the like. Polymeric materials can be processed easily and exhibit properties such as antithrombogenetic activity, biocompatibility and the like. Of these polymeric materials, elastic materials such as segmented polyurethane are preferably used in artificial blood vessels, artificial hearts, insulation coatings of pacemaker leads and the like because of their excellent mechanical properties and high compatibility with biological tissues.

In spite of these excellent properties as implantation materials, the long-term stability of polymeric materials in the living body is inferior to that of other materials because polymeric materials are apt to decompose or degrade in the living body, thus causing problems such as decrease in the mechanical strength, eluation of decomposed compounds and the like. Also, in the case of elastic, soft or hydrophilic materials, they have flexible polymer chains and, as a result, have a higher possibility of degradation and decomposition in comparison with hard materials. Decomposition and degradation in the living body depends also on the shape of the material and increases when the material has a large surface area. As a consequence, when polymeric materials are made into thin film, porous and similar implantation materials making use of their flexibility, it is highly probable that the degree of the decomposition and degradation of the resulting implants is high.

To date, a method for effectively inhibiting biological decomposition and degradation of polymeric materials has not been found, thus preventing the full utilization of the benefits of polymeric materials.

SUMMARY OF THE INVENTION

The present inventors have considered the above-mentioned problems and have conducted intensive studies on the development of a method for inhibiting biological decomposition and/or degradation of polymeric materials for implantation in the living body. They have unexpectedly found that dipyridamole and/or a salt thereof or a derivative thereof, which have been known as a vasodilator and as a platelet adhesion inhibitor, possess a markedly excellent effect in inhibiting biological decomposition and/or degradation of polymeric materials.

An object of the present invention is to provide a method for inhibiting decomposition and/or degradation of an implantation polymeric material in a living body, which comprises applying dipyridamole and/or a salt and/or derivative thereof as an active component in the vicinity of the implantation polymeric material implanted in the living body.

Another object of the present invention is to provide an inhibitor effective for inhibiting biological decomposition and/or degradation of a polymeric material implanted in the living body, which comprises dipyridamole and/or a salt and/or derivative thereof as an active component.

Yet another object of the present invention is to provide an implantation polymeric material which contains dipyridamole and/or a salt or derivative thereof as an active component.

DETAILED DESCRIPTION OF THE INVENTION

Biological decomposition and degradation include any changes of an implanted material in its material characteristics such as mechanical or chemical characteristics, which are generated by biological reactions such as immune system reactions, inflammatory reactions and the like that occur when a material is implanted in the living body.

Implantation material includes any material implanted in the living body for a certain period of time. The implantation period varies depending on its purpose, generally from several days to several decades. Typical examples of the implantation materials include, but are not limited to,: surgical materials such as a suture, an adhesive material and the like; diagnostic materials such as an indwelling sensor and the like; tissue prostheses such as artificial skin, an artificial muscle, a gap filler and the like; dental materials such as an artificial tooth, an artificial root and the like; orthopedic materials such as an artificial joint, an artificial bone and the like; implantation type artificial organs such as an artificial kidney, an artificial lung, an artificial liver, an artificial pancreas and the like; materials for a circulatory organ use such as an artificial blood vessel, an artificial heart, a prosthetic cardiac valve, insulation coating of pacemaker leads and the like; ophthalmic materials such as an intraocular lens, an artificial cornea and the like; and an indwelling catheter, an indwelling device for drug delivery and the like.

Of these implantation materials, the present invention may be applied most preferably to those with direct contact with blood, such as materials for circulatory organ use, artificial organs and intravascular indwelling catheters.

Implantation of polymeric material should be interpreted to include a portion or a whole of any of the above implantation materials, which is composed of one or a plurality of polymeric materials.

Polymeric material should be interpreted to include any generally defined polymer as disclosed for instance in Koubunshi Kagaku (S. Murahashi et al., Kyoritsu Shuppan) and Koubunshi Kagaku Joron (S. Okamura et al., Kagaku Dojin). From a chemical point of view, a polymeric material is a compound which is composed of repeating units linked by carbon-to-carbon, ester, ether, urethane, amide, urea, imide, carbonate, sulfone, siloxane and the like bonds or linkages. Each polymeric material may be composed of the same or two or more different types of repeating units, bonds or linkages. In other words, the polymeric material may be a homopolymer or a copolymer, and the latter may be selected from a random copolymer, an alternating copolymer, a block copolymer, a graft copolymer and the like.

Also, the polymeric material may have a linear or a cross-linked structure. The cross-linking may be effected by chemical bonding or by physical interactions such as hydrogen bonding, ionic bonding, hydrophobic bonding, crystallization and the like. Polypeptides which are polymers of amino acids are also included in polymeric materials.

Typical examples of such polymeric materials include: vinyl polymers such as polyethylene, polypropylene, polybutadiene, polystyrene, polyvinyl alcohol, an ethylenevinyl alcohol copolymer, polymethyl methacrylate, polyhydroxyethyl methacrylate, polyacrylamide, polydimethylacrylamide, polyvinyl chloride, polyethylene fluoride, polypropylene fluoride and the like; polyesters such as polyethylene terephthalate, polybutylene terephthalate and the like; segmented polyesters such as a polytetramethylene glycol-polyethylene terephthalate block copolymer, a polycaprolactone-polyethylene terephthalate block copolymer and the like; polyethers such as polyethylene glycol, polypropylene glycol, polyoxymethylene, polyphenylene oxide, polysaccharide and the like; polyurethanes such as polyether urethane, polyester urethane, polyether urethane urea, polyester urethane urea and the like; segmented linear thermoplastic polyurethanes; polyamides such as nylon and the like; polysiloxanes such as polydimethylsiloxane and the like; and polycarbonates, polysulfones and the like.

The present invention may be most effectively applied to soft and elastic polymeric materials, as well as hydrophilic polymeric materials, whose polymer chains are flexible and which are sensitive to biological degradation.

Typical examples of such preferred polymeric materials include: amorphous polymer chains having low glass transition temperature, such as polyisoprene, polybutadiene, polypropylene oxide, polyethylene oxide, polytetramethylene glycol and the like; and polymeric materials which contain hydrophilic polymer chains in their molecules, such as polyacrylamide, polyvinyl alcohol, polyvinyl pyrrolidone, polysaccharide, polypeptide and the like. Each of these polymeric materials may have a cross-linked structure effected by the aforementioned means or may be used in combination with other polymeric materials.

Thermoplastic elastomer is a preferred example of these polymeric materials. In contrast to the usual elastic polymeric materials, thermoplastic elastomer is a linear polymer which is composed of a so-called "hard segment" having high crystallinity and a so-called "soft segment" having high flexibility. It has no intermolecular chemical cross-linking, and its shape is kept by the aggregation of the hard segment. As a consequence, physical properties of the thermoplastic elastomer are reduced by degradation and decomposition more quickly than as is the case of the usual cross-linked elastic materials. In general, the thermoplastic elastomer consisting of such hard and soft segments frequently forms a micro phase separation structure in which these segments are microscopically separated from each other. When these separated segments are respectively hydrophobic and hydrophilic, the elastomer shows excellent anti-thrombogenetic activity and therefore is used most desirably as an implantation material which is in direct contact with blood, such as an artificial blood vessel and the like. Though not particularly limited, a segmented polyurethane, a segmented polyester and the like may be included in typical examples of such polymeric materials.

The polymeric material of the present invention forms a portion or the whole of an implantation material, and formation of a portion of the implantation material with a polymer may be effected making use of coating, application, adhesion, kneading, embedding, lamination and the similar means.

Dipyridamole, which is used as an active component having activities which inhibit biological decomposition and/or degradation of the implantation polymeric materials of the present invention, is a generic name for 2,6-dis(diethanolamino)-4,8-dipiperidinopyrimido [5,4-d]pyrimidine, represented by formula (I):

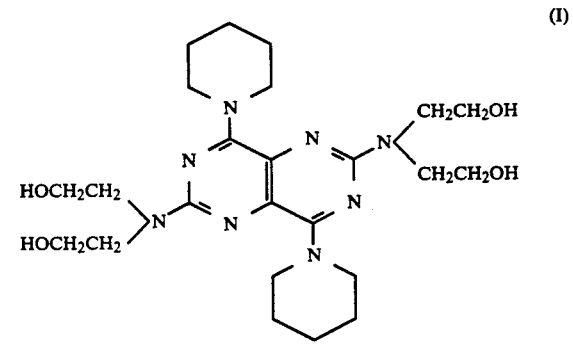

or salts thereof. Illustrative examples of salts of dipyridamole include sulfite, bis(phosphonoxy) propionate, sulfate, p-toluenesulfonate, phosphate, guanosine 5'-monophosphates, inosine 5'-monophosphates, adenosine phosphates, diphosphoglycerate and the like.

It is known that dipyridamole has many useful functions including thromboembolism inhibition, platelet aggregation inhibition, platelet adhesion inhibition, platelet activation inhibition, urinary protein reduction, vasodilation and the like. Because of these functions, dipyridamole has been used as a postoperative thromboembolism inhibitor and a nephrotic syndrome therapeutic agent. However, its effect to inhibit biological decomposition and/or degradation of polymeric materials, as disclosed in the present invention, is unexpected in view of the prior art in regard to the function and effect of dipyridamole. Known polymeric materials which have not been practically employed as an implantation materials become usable therefor when used with the dipyridamole and/or a salt and/or a derivative thereof.

Administration of dipyridamole and/or a salt and/or a derivative thereof into the living body may be effected by any of common administration including oral administration, gastrointestinal administration such as rectal instillation and the like, intravascular administration such as intravenous injection, intraarterial injection and the like, subcutaneous injection, intramuscular injection, intraperitoneal injection, application and the like, as well as tissue administration by indwelling of microcapsules and the like. The dipyridamole and/or a salt and/or a derivative thereof can be formulated into a pharmaceutical composition together with known pharmaceutically acceptable carrier. Effect of the dipyridamole and/or a salt and/or a derivative thereof may be obtained by administering the compound in such an amount that it exists in a sufficient amount in the vicinity of the implantation polymeric material of interest. For example, in the case of oral administration, a preferred dose of the compound per day may be 1 mg/kg body weight or more but less than 20 mg/kg body weight. More specifically, the dipyridamole and/or a salt and/or a derivative thereof may be formulated into Persantin tablets (manufactured by Behringer-Tanabe) for oral administration in an amount of 100 mg/tablet. It may be also formulated into an injectable solution in an amount of 100 mg/2 ml.

The implantation polymeric material of the present invention may contain dipyridamole and/or a salt and/or a derivative thereof in an amount of from 0.0001 to 100% by weight, preferably from 0.001 to 50% by weight of the implantation polymeric material, although the amount may vary because the necessary amount of the compound changes depending on the shape, raw material, used portion and the like.

In the case of a polyurethane artificial blood vessel which contains dipyridamole and/or a salt or a derivative thereof, the compound may be used in an amount of from 0.0001 to 100% by weight, preferably from 0.001 to 50% by weight, more preferably from 0.01 to 10% by weight, based on the weight of urethane. If the amount of the compound is smaller than 0.0001% by weight, this reduces the effect of the compound to inhibit biological decomposition. If the amount of the compound is larger than 100% by weight, this results in inferior mechanical properties and patency as a blood vessel.

In regard to an illustrative mode of an implantation polymeric material which contains dipyridamole, the dipyridamole may be included in the polymeric material or, if the material for implantation has a porous structure, the compound may be kept in pores of the material.

In the former case, the polymeric material may be kneaded with dipyridamole. In that instance, dipyridamole may be dispersed or dissolved in a solution of the polymeric material, or, in the case of a thermoplastic polymeric material, dipyridamole may be dispersed in a solution of the thermoplastic polymeric material or the material and the compound may be made into a mixed melting solution when the material has a higher melting point than that of the compound (about 165° C).

In the latter case, the material for implantation use having a porous structure may be soaked in a solution of dipyridamole, thus allowing the dipyridamole solution to permeate into the pores of the material, and then the solvent may be removed by distillation thereby keeping dipyridamole molecules inside the pores. The type of solvent for use in the above purpose varies depending on the polymeric material to be used. Examples of a preferable solvent of dipyridamole include methanol, ethanol, chloroform, dioxane and a dilute acid having a pH value of 3.3 or below. A commercial parenteral solution may also be used.

It is assumed that the effective inhibition of the decomposition of the implantation polymeric material of the present invention is attained through the release of dipyridamole and/or a salt or a derivative thereof from the surface of the polymeric material after its implantation in the living body.

Although the implantation polymeric material of the present invention itself possesses a resistant feature to its decomposition in the living body, it is preferable to use it together with the administration of dipyridamole and/or a salt or a derivative thereof. By the joint use of the compound with the implantation polymeric material and the administration of the compound into the living body, decomposition of the implanted polymeric material in the living body can be inhibited more efficiently.

EXAMPLES

To further illustrate the present invention in greater detail, the following examples are given, but are not to be construed as to limit the scope of the invention.

PRODUCTION EXAMPLE 1

4,4'-diphenylmethane diisocyanate (MDI), polytetramethylene glycol (PTMG) having a molecular weight of 1,000 and 1,4-butanediol (1,4-BD) (molar ratio: MDI/PTMG/1,4-BD=2/1/1) were polymerized by a prepolymer process in a mixed solvent of N,N-dimethylacetamide (DMAc) and 1,4-dioxane (weight ratio: DMAc/dioxane=7/3) to obtain a segmented polyurethane.

The segmented polyurethane thus prepared was purified by subjecting it to Soxhlet extraction with ethanol for 3 hours.

PRODUCTION EXAMPLE 2

The purified segmented polyurethane obtained in Production Example 1 was mixed with the same weight of NaCl crystals having a particle size of about 50 μm, and the mixture was dissolved in a mixed solvent of DMAc and 1,4-dioxane (weight ratio: DMAc/dioxane=1:1) to obtain a solution containing 30% by weight of polyurethane (to be referred to as "dope" hereinafter). The thus prepared dope was spread on a glass dish and, after adding an appropriate amount of water for injection, was allowed to stand for overnight to coagulate and precipitate into the thus treated polyurethane.

A film of the thus formed polymer was detached from the glass dish and washed with water thoroughly to remove NaCl, thereby obtaining a porous film of segmented polyurethane having a thickness of 1.5 mm.

PRODUCTION EXAMPLE 3

A dope was prepared in the same manner as in Production Example 2. A glass rod having an outer diameter of 3 mm was soaked in the thus prepared dope and then removed to coat the rod with the dope. The coated glass rod was soaked overnight in purified water to coagulate and precipitate segmented polyurethane. Thereafter, a tubular form of segmented polyurethane was detached from the glass rod and then washed thoroughly with purified water to remove NaCl and remaining solvent. The tubular form of segmented polyurethane (to be referred to as "artificial blood vessel" hereinafter) was a tube of 3 mm in inner diameter and 4.5 mm in outer diameter having a porous structure which contained communicating pores through inner and outer surfaces of the tube.

PRODUCTION EXAMPLE 4

95 parts by weight of the purified segmented polyurethane obtained in Production Example 1 was mixed with 5 parts by weight of dipyridamole, and the mixture was dissolved in a mixed solvent of DMAc and 1,4-dioxane (weight ratio: DMAc/dioxane=1:1). The resulting solution was mixed thoroughly with NaCl crystals (2.6 times as weigh as the weight of the segmented polyurethane) having a particle size of about 50 μm as a pore-forming material, thereby obtaining a dope containing 15% by weight of polyurethane for use in the preparation of an artificial blood vessel.

A glass rod having an outer diameter of 3 mm was soaked in the thus prepared dope and then removed to coat the rod with the dope. The coated glass rod was soaked overnight in purified water to coagulate and precipitate the segmented polyurethane. Thereafter, a tubular form of the segmented polyurethane was detached from the glass rod and then washed thoroughly with purified water to remove NaCl and remaining solvent. The tubular form of segmented polyurethane (to be referred to as "artificial blood vessel" hereinafter) was a tube of 3 mm in inner diameter and 4.5 mm in outer diameter having a porous structure which contained communicating pores through inner and outer surfaces of the tube.

PRODUCTION EXAMPLE 5

As a comparative example, the process of Production Example 4 was performed except that dipyridamole was not used, thereby obtaining an artificial blood vessel which does not contain dipyridamole (a porous segmented polyurethane tube of 3 mm in inner diameter and 4.5 mm in outer diameter containing communicating pores through inner and outer surfaces of the tube).

PRODUCTION EXAMPLE 6

A dope prepared in the same manner as in Production Example 4 was spread on a glass dish and, after adding an appropriate amount of water for injection, allowed to stand for overnight to coagulate and precipitate into the thus treated polyurethane.

A film of the polymer thus formed was detached from the glass dish and washed with water thoroughly to remove NaCl, thereby obtaining a porous film of segmented polyurethane having a thickness of 1.5 mm.

PRODUCTION EXAMPLE 7

As a comparative example, the process of Production Example 6 was performed except that dipyridamole was not used, thereby obtaining a porous film of segmented polyurethane having a thickness of 1.5 mm which does not contain dipyridamole.

PRODUCTION EXAMPLE 8

The porous segmented polyurethane tube obtained in Production Example 5 (about 3 cm in length) was soaked in an ethanol solution containing 10% by weight of dipyridamole, and the dipyridamole solution was allowed to permeate thoroughly into the pores of the tube under reduced pressure using a vacuum pump. Thereafter, the treated tube was removed from the dipyridamole solution and dried under a reduced pressure to obtain an artificial blood vessel which contained dipyridamole in its pores (a porous segmented polyurethane tube of 3 mm in inner diameter and 4.5 mm in outer diameter containing communicating pores through inner and outer surfaces of the tube).

PRODUCTION EXAMPLE 9

The porous segmented polyurethane film obtained in Production Example 7 (approximately 2 cm × 2 cm) was treated in the same manner as in Production Example 8 to obtain a porous segmented polyurethane film which contained dipyridamole in its pores.

EXAMPLE 1

The porous segmented polyurethane film obtained in Production Example 2 (approximately 2 cm × 2 cm) was subcutaneously implanted into crossbred adult dogs which were divided into a dipyridamole-administered group and a control group (no administration of the compound). After three months of the implantation, the films were recovered to measure changes in their molecular weights by gel permeation chromatography and to compare the results between the two test groups. In the dipyridamole-administered group, oral administration of dipyridamole was started one week before the implantation operation and continued until the day of the film removal at dose of 10 mg/kg body weight/day. Dipyridamole was formulated into Persantin tablet (100 mg/tablet, manufactured by Behringer-Tanabe). In the control group, dipyridamole was not administered during this period.

The polystyrene-based molecular weight of the film, which was 150,000 when measured by gel permeation chromatography before the implantation, was reduced to 100,000 after the implantation in the control group, while no decrease in the molecular weight was found in the dipyridamole-administered group after the implantation.

EXAMPLE 2

The artificial blood vessel obtained in Production Example 3 (approximately 5 cm in length) was transplanted to the femoral artery of crossbred adult dogs which were divided into a dipyridamole-administered group and a control group which were not administered the compound. Three months following the transplantation, the artificial blood vessels were recovered to measure changes in their molecular weights by gel permeation chromatography and to compare the results between the two test groups. In the dipyridamole-administered group, oral administration of dipyridamole in the same dosage form as in Example 1 was started one week before the transplantation operation and continued until the day of the film removal at a dose of 10 mg/kg body weight/day. In the control group, dipyridamole was not administered during this period.

The polystyrene-based molecular weight of the artificial blood vessel-constituting segmented polyurethane, which was 150,000 when measured by gel permeation chromatography before the transplantation, was reduced to 90,000 after the transplantation in the control group, while no decrease in the molecular weight was found in the dipyridamole-administered group after the implantation.

EXAMPLE 3

The artificial blood vessel made of the dipyridamole-containing segmented polyurethane (approximately 3 cm in length) obtained in Production Example 4, was transplanted to the femoral artery of crossbred adult dogs which were used as a test group. As a comparative example, the artificial blood vessel made of the dipyridamole-free segmented polyurethane (approximately 3 cm in length) obtained in Production Example 5, was transplanted to the femoral artery of other crossbred adult dogs which were used as a control group. After six months following the transplantation, the artificial blood vessels were recovered to measure changes in the molecular weight of the artificial blood vessel-constituting segmented polyurethane by gel permeation chromatography and to compare the results between the two groups. Additional administration of dipyridamole was not carried out during the transplantation period.

The polystyrene-based molecular weight of each of the segmented polyurethane portions of the artificial blood vessels, which was 150,000 when measured by gel permation chromatography before the transplantation, was reduced to 100,000 after six months of the transplantation in the case of the control group in which the artificial blood vessel made of the dipyridamole-free segmented polyurethane of Production Example 5 was used as a comparative example. In contrast, the molecular weight of the artificial vessel made of the dipyridamole-mixed segmented polyurethane did not decrease even following six months after the transplantation.

EXAMPLE 4

The dipyridamole-containing porous segmented polyurethane film (approximately 2 cm×2 cm) obtained in Production Example 6 was subcutaneously implanted in crossbred adult dogs which were used as a test group. As a comparative example, the dipyridamole-free porous segmented polyurethane film (approximately 2 cm×2 cm) obtained in Production Example 7 was subcutaneously implanted in other crossbred adult dogs which were used as a control group. After three months following the implantation, the films were recovered to measure changes in their molecular weights by gel permeation chromatography and to compare the results between the two groups. Additional administration of dipyridamole was not carried out during the transplantation period.

The polystyrene-based molecular weight of each of the films, which was 150,000 when measured by gel permeation chromatography before the implantation, was reduced to 110,000 after three months of the implantation in the case of the control group in which the dipyridamole-free film was used as a comparative example. In contrast, the molecular weight of the dipyridamole-containing film did not decrease even after three months of the implantation.

EXAMPLE 5

The artificial blood vessel having dipyridamole-included pores (approximately 3 cm in length) obtained in Production Example 8 was transplanted into the femoral artery of crossbred adult dogs which were used as a test group. As a comparative example, the artificial blood vessel made of the dipyridamole-free segmented polyurethane (approximately 3 cm in length) obtained in Production Example 5, was transplanted into the femoral artery of other crossbred adult dogs which were used as a control group. Six months following the transplantation, the artificial blood vessels were recovered to measure changes in the molecular weight of the artificial blood vessel-constituting segmented polyurethane by gel permeation chromatography and to compare the results between the two groups. Additional administration of dipyridamole was not carried out during the transplantation period.

The polystyrene-based molecular weight of each of the segmented polyurethane portions of the artificial blood vessels, which was 150,000 when measured by gel permeation chromatography before the transplantation, was reduced to 100,000 after six months of the transplantation in the case of the control group in which the artificial blood vessel made of the dipyridamole-free segmented polyurethane of Production Example 5 was used as a comparative example. In contrast, the molecular weight of the artificial vessel made of the dipyridamole-included segmented polyurethane did not decrease even after six months following the transplantation.

EXAMPLE 6

The porous segmented polyurethane film having dipyridamole-included pores (approximately 2 cm×2 cm) obtained in Production Example 9 was subcutaneously implanted in crossbred adult dogs which were used as a test group. As a comparative example, the dipyridamole-free porous segmented polyurethane film (approximately 2 cm×2 cm) obtained in Production Example 7 was subcutaneously implanted in other crossbred adult dogs which were used as a control group. After three months following the implantation, the films were recovered to measure changes in their molecular weights by gel permeation chromatography and to compare the results between the two groups. Additional administration of dipyridamole was not carried out during the transplantation period.

The polystyrene-based molecular weight of each of the films, which was 150,000 when measured by gel permeation chromatography before the implantation, was reduced to 110,000 after three months following the implantation in the case of the control group in which the dipyridamole-free film was used as a comparative example. In contrast, the molecular weight of the dipyridamole-containing film did not decrease even after three months following the implantation.

By locating dipyridamole and/or a salt or a derivative thereof in the vicinity of the presently claimed implantation polymeric material implanted in the living body, biological decomposition or degradation of the implanted polymeric material can be effectively inhibited, thereby allowing possible improvement of the durability and safety of the material.

While the invention has been described in detail and with reference to specific examples thereof, it will be apparent to one skilled in the art that various changes and modifications can be made therein without departing from the spirit and scope thereof.

What is claimed is:

1. A method for inhibiting decomposition or degradation of an polyurethane implantation material in a living body, comprising administering to the living body in the vicinity of said polyurethane implantation polymeric material implanted in the living body, a composition comprising:
    (a) an effective amount of at least one member selected from the group consisting of dipyridamole, dipyridamole derivative and salts of said dipyridamole and dipyridamole derivatives, as an active component; and
    (b) a pharmaceutically acceptable carrier.

2. An implantation polymeric material which exhibits minimal biological decomposition or degradation and contains one member selected from the group consisting of dipyridamole, dipyridamole derivatives and salts of said dipyridamole and dipyridamole derivatives, as an active component.

3. The implantation polymeric material according to claim 2, wherein a portion or a whole of said polyurethane material comprises soft and elastic polymeric materials.

4. The implantation polymeric material according to claim 2, wherein a portion or a whole of said material comprises a segmented polyurethane.

5. The polyurethane implantation material according to claim 2, wherein said material is applied to a blood-contacting part.

6. An artificial blood vessel which is prepared from the implantation polymeric material of claim 2.

7. An artificial blood vessel which is prepared from the implantation polymeric material of claim 3.

8. An artificial blood vessel which is prepared from the implantation polymeric material of claim 4.

9. The method for inhibiting decomposition or degradation of an polyurethane implantation material in the living body as recited in claim 1, wherein said composition is administered orally in an amount of 1 mg/kg to 20 mg/kg body weight daily.

10. The polyurethane implantation material, as recited in one of claims 2-5, wherein said active component is present in an amount of 0.0001-100% by weight of said polyurethane implantation polymeric material.

11. The polyurethane implantation material, as recited in claim 10, wherein said active component is present in an amount of 0.001-50% by weight of said polyurethane implantation polymeric material.

12. The artificial blood vessel as recited in claim 8, wherein said active component is present in an amount of 0.0001-100% by weight of said polyurethane implantation polymeric material.

13. The artificial blood vessel as recited in claim 12, wherein said active component is present in an amount of 0.001-50% by weight of said polyurethane implantation polymeric material.

14. The artificial blood vessel as recited in claim 13, wherein said active component is present in an amount of 0.01-10% by weight of said polyurethane implantation polymeric material.

15. A method for inhibiting decomposition or degradation of the artificial blood vessel made of segmented polyurethane in a living body, which comprises administering to the living body in the vicinity of said artificial blood vessel implanted in the living body, a composition comprising:

(a) an effective amount of at least one member selected from the group consisting of dipyridamole, dipyridamole derivatives and salts of said dipyridamole and dipyridamole derivatives, as an active component; and (b) a pharmaceutically acceptable carrier.

16. A method for inhibiting decomposition or degradation of the artificial blood vessel as recited in claim 8 in a living body, comprising administering to the living body in the vicinity of said artificial blood vessel implanted in the living body, a composition comprising:

(a) an effective amount of at least one member selected from the group consisting of dipyridamole, dipyridamole derivatives and salts of said dipyridamole and dipyridamole derivatives, as an active component; and (b) a pharmaceutically acceptable carrier.

* * * * *